US012740960B2

(12) United States Patent
Wickenhauser et al.

(10) Patent No.: US 12,740,960 B2
(45) **Date of Patent: *Sep. 22, 2026**

(54) TREATMENT OF HERPES ZOSTER WITH TOPICAL TETRACAINE

(71) Applicant: PAGARI LIFE SCIENCE CORP, Bethalto, IL (US)

(72) Inventors: Alan J. Wickenhauser, Moro, IL (US); Stephen E. Peipert, Edwardsville, IL (US)

(73) Assignee: PAGARI LIFE SCIENCE CORP, Bethalto, IL (US)

( * ) Notice: Subject to any disclaimer, the term of this patent is extended or adjusted under 35 U.S.C. 154(b) by 499 days.

This patent is subject to a terminal disclaimer.

(21) Appl. No.: 18/362,522

(22) Filed: Jul. 31, 2023

(65) Prior Publication Data

US 2024/0197670 A1 Jun. 20, 2024

Related U.S. Application Data

(63) Continuation-in-part of application No. 18/068,403, filed on Dec. 19, 2022, now Pat. No. 12,201,600.

(51) Int. Cl.

| | |
|---|---|
| ***A61K 31/245*** | (2006.01) |
| ***A61K 9/00*** | (2006.01) |
| ***A61K 47/10*** | (2017.01) |
| ***A61K 47/38*** | (2006.01) |
| ***A61P 31/22*** | (2006.01) |

(52) U.S. Cl.

CPC .......... *A61K 31/245* (2013.01); *A61K 9/0014* (2013.01); *A61K 47/10* (2013.01); *A61K 47/38* (2013.01); *A61P 31/22* (2018.01)

(58) Field of Classification Search

CPC ........ A61P 17/02; A61P 31/22; A61K 31/245; A61K 47/06; A61K 47/10; A61K 47/38; A61K 9/0014; A61K 9/06

See application file for complete search history.

(56) References Cited

U.S. PATENT DOCUMENTS

| | | | | |
|---|---|---|---|---|
| 5,696,160 | A | 12/1997 | Miller et al. | |
| 8,263,047 | B2 | 9/2012 | Wickenhauser et al. | |
| 8,623,334 | B1 | 1/2014 | Wickenhauser et al. | |
| 8,968,710 | B1 | 3/2015 | Wickenhauser et al. | |
| 10,682,370 | B2 * | 6/2020 | Ryoo | A61K 47/32 |

FOREIGN PATENT DOCUMENTS

| | | | |
|---|---|---|---|
| CN | 1221264 | C | 10/2005 |
| CN | 114209720 | A | 3/2022 |
| WO | 2011028629 | A1 | 3/2011 |
| WO | 2012064766 | A2 | 5/2012 |

OTHER PUBLICATIONS

International Search Report and Written Opinion in International Patent Application No. PCT/US2023/084790, dated Apr. 5, 2024, in 14 pages.

Lidocaine and Tetracaine Cream to Treat Postherpetic Neuralgia (PHN), NCT00609323, ClinicalTrials.gov, Oct. 29, 2022 (6 pages).

Carn, Bradley , et al., "Achieving pulpal anesthesia with a topical anesthetic paste", Journal of Orofacial Sciences, 2015, 7:2:125-128.

Christa, Hopp , et al., "Clinical efficacy of tetracaine anesthetic paste", Gen Dent, Mar.-Apr. 2012, 60(2):e69-73, abstract only.

Kaminester, Lewis H, et al., "A Double-blind, Placebo-controlled Study of Topical Tetracaine in the Treatment of Herpes Labialis", J. Am. Acad Dermatol, May 17, 1999, 41:6:996-1001.

Miller, K.J. , et al., In Vitro Transdermal Diffusional Properties of Tetracaine from a Topical Formulation, 21 pages.

Miller, K.J. , et al., "Solubility and in vitro Percutaneous Absorption of Tetracaine from Solvents of Propylene Glycol and Saline", International Journal of Pharmaceutics, 1993, 98:101-111.

Riopelle , et al., "Treatment of the cutaneous pain of acute herpes zoster with 9% lidocaine (base) in petrolatum/paraffin ointment", J. American Academy of Dermatology, 1994, vol. 30, Issue 5, Part 1, pp. 757-767 (Year: 1994).

Yamanaka, Daiki , et al., "Peripheral nerve block with a high concentration of tetracaine dissolved in bupivacaine for intractable post-herpetic itch: a case report", Yamanaka et al. JA Clinical Reports (2016) 2:43.

* cited by examiner

*Primary Examiner* — Umamaheswari Ramachandran

(74) *Attorney, Agent, or Firm* — DUANE MORRIS LLP

(57) ABSTRACT

The present invention relates to a method of treating herpes zoster (shingles), such as in the acute eruptive phase, or deactivating varicella zoster virus (the virus that causes herpes zoster), such as an in a patient suffering from herpes zoster, comprising topically administering tetracaine base (or a pharmaceutically acceptable salt thereof) to a patient in need of such treatment.

18 Claims, 10 Drawing Sheets

FIG. 1
Day 0
Day 1
Day 2
Day 3
Day 4
Day 5
Day 7

TREATMENT OF HERPES ZOSTER WITH TOPICAL TETRACAINE

This application is a continuation-in-part application of U.S. application Ser. No. 18/068,403, filed on Dec. 19, 2022, the entire contents of which are hereby by incorporated by reference.

FIELD OF THE INVENTION

The present invention relates to a method of treating herpes zoster (shingles) comprising topically administering tetracaine base (or a pharmaceutically acceptable salt thereof) to a patient in need of such treatment. The present invention also relates to a method of deactivating varicella zoster virus (the virus that causes herpes zoster) comprising topically administering tetracaine base (or a pharmaceutically acceptable salt thereof) to a patient in need of such treatment.

BACKGROUND OF THE INVENTION

Approximately one million people in the United States are diagnosed with shingles, herpes zoster, each year. This viral disease is premised by a primary infection with varicella zoster (chicken pox) and is caused by a reactivated replication of a dormant virus that resides in ganglionic nerves.

The risk of shingles increases with age, and individuals with compromised immune systems may be particularly vulnerable. The disease comprises three phases: a pre-eruptive phase characterized by a multitude of sensory nerve phenomena, which may last 48-72 hours; an acute eruptive phase characterized by lesions, mild to severe pain, pruritus, and hyperesthesia, which may last 2-4 weeks; and a chronic phase characterized by post-herpetic neuralgia (PHN), which may persist 3-6 months or longer and may affect approximately 20% of shingles patients.

Two zoster vaccines have been approved in the United States. Shingrix, marketed by GlaxoSmithKline, is a recombinant subunit vaccine which has been used in many countries since 2017. Shingrix is a suspension for intramuscular injection indicated for the prevention of herpes zoster in adults aged 50 years and older, and in adults aged 18 years or older who are or will be at increased risk of herpes zoster due to immunodeficiency or immunosuppression caused by known disease or therapy. The Singrix vaccine has various side effects such as pain at the injection site, redness, swelling, muscle pain, fatigue, and a possibility of causing Guillain Barre Syndrome (which FDA required a warning of in 2021).

Zostavax (Merck), in use since 2006, is an attenuated vaccine which consists of a larger-than-normal dose of chickenpox vaccine. Zostavax was discontinued in the United States in November 2020.

Tetracaine, also known as amethocaine, is an ester local anesthetic used to numb the eyes, nose, or throat. It may also be applied to the skin before starting an intravenous (injection) to decrease pain from the procedure.

U.S. Pat. Nos. 8,263,047, 8,623,334, and 8,968,710 disclose a topical anesthetic for dental procedures containing about 3 wt. % to 10 wt. % tetracaine in a vehicle suitable for administration to the oral mucosa. Kaminester et al., *J. Am. Acad. Dermatol.,* 41(6), 996-1001, 1999, describes the result of a double blind, placebo-controlled study of topical tetracaine in the treatment of herpes labialis. Yamanaka et al., *JA Clinical Reports,* 2(43), 1-4, 2016, describes a case report study of peripheral nerve block using tetracaine dissolved in bupivacaine for intractable post-herpetic itch. Pliaglis®, a topical cream containing lidocaine and tetracaine (7%/7%), is indicated for use on intact skin in adults to provide topical local analgesia for superficial dermatological procedures such as dermal filler injection, pulsed dye laser therapy, facial laser resurfacing, and laser-assisted tattoo removal, and has been studied for the treatment of postherpetic neuralgia (PHN) (NCT00609323).

There is a need for new methods and compositions for the treatment and/or prevention of herpes zoster, for example, methods that do not involve intramuscular injection. The present invention addresses such needs.

SUMMARY OF THE INVENTION

The present inventor has surprisingly found that topical administration of tetracaine base is effective in the treatment of herpes zoster and deactivation of varicella zoster virus (the virus that causes herpes zoster), including when herpes zoster is in its active eruptive phase. One advantage of the methods described herein is that they avoid the need for the existing vaccines which have side effects including an elevated risk of Guillain Barré Syndrome.

One embodiment is a method of treating herpes zoster in a patient in need thereof (such as a patient in the active eruptive phase of herpes zoster) by topically administering to the patient a composition comprising from about 2 wt. % to about 10 wt. % of tetracaine base (or a pharmaceutically acceptable salt thereof such as tetracaine hydrochloride), based on the 100% total weight of the composition.

Another embodiment is a method of deactivating varicella zoster virus in a patient in need thereof (such as a patient in the active eruptive phase of herpes zoster) by topically administering to the patient an effective amount of tetracaine base (or a pharmaceutically acceptable salt thereof such as tetracaine hydrochloride). In one embodiment, the patient suffers from herpes zoster. In another embodiment, the patient is in the active eruptive phase of herpes zoster. In one embodiment, the tetracaine is administered with a composition comprising from about 2 wt. % to about 10 wt. % of tetracaine base (or a pharmaceutically acceptable salt thereof such as tetracaine hydrochloride), based on the 100% total weight of the composition. The composition may be in the form of a cream or an ointment.

Yet another embodiment is a method of deactivating varicella zoster virus in a patient in need thereof (such as a patient in the active eruptive phase of herpes zoster) by topically administering to the patient a composition comprising from about 2 wt. % to about 10 wt. % of tetracaine base (or a pharmaceutically acceptable salt thereof such as tetracaine hydrochloride), based on the 100% total weight of the composition. In one embodiment, the patient suffers from herpes zoster. In another embodiment, the patient is in the active eruptive phase of herpes zoster.

In one embodiment, the patient is in the active eruptive phase of herpes zoster when initially administered the composition.

Yet another embodiment is a method of treating herpes zoster in the active eruptive phase in a patient in need thereof by topically administering to the patient a composition comprising from about 2 wt. % to about 10 wt. % of tetracaine base (or a pharmaceutically acceptable salt thereof such as tetracaine hydrochloride), based on the 100% total weight of the composition.

Yet another embodiment is a method of deactivating varicella zoster virus in a patient in need thereof, where the patient is in the active eruptive phase of herpes zoster, by topically administering to the patient a composition comprising from about 2 wt. % to about 10 wt. % of tetracaine base (or a pharmaceutically acceptable salt thereof such as tetracaine hydrochloride), based on the 100% total weight of the composition Yet another embodiment is a method of treating lesions associated with herpes zoster in the active eruptive phase in a patient in need thereof by topically administering to the patient a composition comprising from about 2 wt. % to about 10 wt. % of tetracaine base (or a pharmaceutically acceptable salt thereof such as tetracaine hydrochloride), based on the 100% total weight of the composition.

Yet another embodiment is a method of treating one or more symptoms associated with herpes zoster in the active eruptive phase in a patient in need thereof comprising topically administering to the patient a composition comprising from about 2 wt. % to about 10 wt. % of tetracaine base (or a pharmaceutically acceptable salt thereof such as tetracaine hydrochloride), based on the 100% total weight of the composition. The one or more symptoms can be selected from lesions, blisters, rash, mild to severe pain, pruritus, hyperesthesia, and any combination of any of the foregoing. In one embodiment, the symptom treated is lesions. In another embodiment, the symptom treated is blisters. In yet another embodiment, the symptom treated is rash.

In one embodiment of any of the methods described herein, the method comprises topically administering a composition comprising between about 3% and about 10% by weight of tetracaine base (or a pharmaceutically acceptable salt thereof such as tetracaine hydrochloride).

In one embodiment of any of the methods described herein, the composition comprises about 2 wt. % to about 10 wt. % of tetracaine base. In one embodiment of any of the methods described herein, tetracaine base is the sole active ingredient in the composition. In one embodiment of any of the methods described herein, the composition does not contain lidocaine or bupivacaine.

In one embodiment of any of the methods described herein, the only form of tetracaine included in the composition is tetracaine base.

In one embodiment of any of the methods described herein, the composition comprises about 2 wt. % to about 10 wt. % of tetracaine hydrochloride.

In one embodiment of any of the methods described herein, the composition may be in the form of a cream or an ointment.

In certain embodiments of any of the methods described herein, the composition comprises a penetration enhancer (such as propylene glycol or polyethylene glycol), one or more mucoadhesives, and a non-aqueous vehicle (such as a hydrocarbon gel). The composition optionally further comprises a thickening agent and/or an odor masking agent.

In certain embodiments of any of the methods described herein, the composition comprises a carrier comprising a non-aqueous vehicle. In certain embodiments of any of the methods described herein, the non-aqueous vehicle comprises a high molecular weight poly(ethylene oxide) homopolymer, a cellulose polymer, propylene glycol, and a plasticized hydrocarbon gel. In certain embodiments of any of the methods described herein, the non-aqueous vehicle comprises a high molecular weight poly(ethylene oxide) homopolymer, a cellulose polymer, polyethylene glycol, and a plasticized hydrocarbon gel.

In certain embodiments of any of the methods described herein, the poly(ethylene oxide) homopolymer has a molecular weight about 4,000,000 Daltons (g/mol).

In certain embodiments of any of the methods described herein, the poly(ethylene oxide) is present in an amount of about 5 wt. % and the cellulose polymer is sodium carboxymethylcellulose and is present in an amount of about 4 wt. %.

In certain embodiments of any of the methods described herein, the propylene glycol is present in an amount of about 5 wt. % to about 15 wt. %.

In certain embodiments of any of the methods described herein, the polyethylene glycol is present in an amount of about 5 wt. % to about 15 wt. %.

In certain embodiments of any of the methods described herein, the composition comprises between about 2% and about 6% by weight of tetracaine base.

In certain embodiments of any of the methods described herein, the composition comprises about 2% by weight of tetracaine base.

In certain embodiments of any of the methods described herein, the composition comprises about 6% by weight of tetracaine base.

In certain embodiments of any of the methods described herein, the patient is suffering from herpes zoster in the acute phase.

In certain embodiments of any of the methods described herein, the composition is topically applied up to three times a day, e.g., once a day, twice a day or three times a day.

In certain embodiments of any of the methods described herein, the patient sees improvement in the symptoms of herpes zoster within about 7 days, within about 5 days or within about 4 days.

In certain embodiments of any of the methods described herein, the patient sees improvement in the symptoms of herpes zoster in less than about 7 days, such as in six days, in five days, or in four days.

In certain embodiments of any of the methods described herein, the composition is topically applied for at least about 10 minutes, such as for about 30 minutes, for about 1 hour, for about 2 hours, for about 4 hours, for about 8 hours, for about 24 hours, for about 48 hours, or for about 72 hours.

DETAILED DESCRIPTION OF THE INVENTION

Figure 1:
FIG. 1 shows the face of the patient described in Example 3 prior to treatment (Day 0) and on Days 1-5 and 7 of treatment with the topical composition of Example 1.
Figure 1:

Tetracaine is a white, or light yellow, waxy solid melting in the range of 41° C. to 46° C. It is very slightly soluble in water, and soluble in alcohol, ether, benzene and chloroform.

In certain embodiments of any of the methods descried herein, the tetracaine is provided in base form, i.e., not as a pharmaceutically acceptable salt, such as the hydrochloride salt.

The term "in need thereof" requires the tetracaine to be administered with the intentional purpose recited, such as for deactivating varicella zoster virus.

In certain embodiments of any of the methods descried herein, the concentration of the tetracaine is from about 2 or 3 wt. % to about 10 wt. % of the total composition, such as from about 2 wt. % to about 6 wt. % of the total composition, e.g., to deliver an effective dosage. In another embodiment of any of the methods descried herein, the concentration of the tetracaine is about 2 wt. % of the total composition. In yet another other embodiment of any of the methods descried herein, the concentration of the tetracaine is about 6 wt. %.

In certain embodiments of any of the methods descried herein, one or more mucoadhesives is included in the composition. As used herein the term mucoadhesive means a natural or synthetic substance, e.g., gels, pastes, macromolecules, polymers, and oligomers, or mixtures thereof, that can adhere to a subject's mucous membrane for a period of time sufficient to locally deliver a therapeutically effective amount of tetracaine. The composition itself need not be mucoadhesive, as long as it can form a mucoadhesive upon on the contact with the mucosa.

Examples of mucoadhesives for use in any of the compositions described herein include, but are not limited to, pectin, alginic acid, chitosan, hyaluronic acid, polysorbates, such as polysorbate-20, -21, -40, -60, -61, -65, -80, -81, -85; polyethylene glycol, such as PEG-7, -14, -16, -18, - 55, -90, -100, -135, -180, -4, -240, -6, -8, -9, -10, -12, -20, or -32; oligosaccharides and polysaccharides, such as gellan, carrageenan, xanthan gum, gum arabic, and dextran; cellulose esters and cellulose ethers; modified cellulose polymers, such as carboxymethylcellulose, sodium carboxymethylcellulose, hydroxyethylcellulose, hydroxypropyl methylcellulose, hydroxyethyl ethylcellulose; polyether polymers and oligomers, such as polyoxyethylene; condensation products of polyethylene oxide with various reactive hydrogen containing compounds having long hydrophobic chains, such as condensation products of poly(ethylene oxide) with fatty acids, fatty alcohols, fatty amides, or polyhydric alcohols; polyether compounds, such as poly(methyl vinyl ether), or polyoxypropylene of less than 10 repeating units; polyether compounds, such as block copolymers of ethylene oxide and propylene oxide; ORABASE7 (a mixture of gelatine, pectin and sodium carboxymethyl cellulose in a plasticized hydrocarbon gel, commercially available from Hoyt laboratories, Needhm, Mass.), or any combination of any of the foregoing.

In certain embodiments of any of the compositions described herein, the mucoadhesive is water soluble and a combination of mucoadhesives is used. For example, homopolymers of ethylene oxide in combination with a second mucoadhesive such as sodium carboxymethylcellulose. Commercially available homopolymers of ethylene oxide are sold under the trademark POLYOX by Dow Chemical Company, Midland, Mich. POLYOX poly(ethylene oxide) polymers have a number of properties for mucoadhesion—namely, water solubility, hydrophilicity, high molecular weight, hydrogen bonding functionality, and good biocompatibility. The polymers have a long linear chain structure which allows them to form a strong interpenetrating network with mucus. In one preferred embodiment, the mucoadhesive includes poly(ethylene oxide) polymers with a molecular weight of 4,000,000 Daltons and higher. The amount of mucoadhesive in the formulation depends upon the mucoadhesives selected and the consistency desired in the composition.

In one embodiment of any of the compositions described herein, the composition comprises sodium carboxymethyl cellulose. In certain embodiments of any of the compositions described herein, the composition comprises between about 1 wt. % and about 10 wt. % sodium carboxymethyl cellulose or between about 3 wt. % and about 5 wt. % sodium carboxymethyl cellulose. In certain embodiments of any of the compositions described herein, the composition comprises between about 4 wt. % sodium carboxymethyl cellulose.

In one embodiment of any of the compositions described herein, the composition comprises POLYOX WSR 301 (a water-soluble, nonionic poly(ethylene oxide) polymer with a molecular weight of 4,000,000 Daltons (g/mol) (available from DuPont) in combination with sodium carboxymethylcellulose (medium viscosity). In one embodiment, the sodium carboxymethylcellulose having medium viscosity has a viscosity in a 2% solution in water at 25° C. of 400-800 cps. In this embodiment, the combined mucoadhesive comprises up to about 10 wt. %, such as about 9 wt. %, of the composition, with POLYOX WSR 301 comprising about 3 wt. % to about 8 wt. %, such as about 5 wt. % of the composition and sodium carboxymethylcellulose comprising about 2 wt. % to about 5 wt. %, such as about 4 wt. % of the composition. In the absence of a mucoadhesive like POLYOX WSR 301, the topical adhesive tends to migrate from the site of application, spreading the therapeutic action of the tetracaine to unintended areas.

In one embodiment of any of the compositions described herein, the composition comprises propylene glycol, for example, as a penetration enhancer to increase the absorption of the tetracaine into the mucosa. Other suitable penetration enhancers may be included. The penetration enhancers should be physicochemically stable and not have pharmacologic effects and preferably should not have disagreeable smell, color or taste. Without limitation, in addition to propylene glycol, other glycols, monohydric alcohols, and fatty acid glycerides may also serve as penetration enhancers. In one embodiment of any of the compositions described herein, the composition comprises polyethylene glycol (e.g., PEG 400), for example, as a penetration enhancer to increase the absorption of the tetracaine into the mucosa. In one embodiment, any of the compositions described herein does not include glycerin.

In one embodiment of any of the compositions described herein, the propylene glycol is present in an amount from about 5 wt. % to 15 wt. %.

In one embodiment of any of the compositions described herein, the polyethylene glycol (e.g., PEG 400) is present in an amount from about 5 wt. % to 15 wt. %.

In one embodiment of any of the compositions described herein, when the poly (ethylene oxide) homopolymer (such as POLYOX WSR 301) is present in an amount of about 5 wt. % and the sodium carboxymethylcellulose is present in an amount of about 4 wt. %, the propylene glycol may be present in an amount of about 10 wt. % as larger amounts of propylene glycol may render the paste too fluid to stay in place at the site of application.

In one embodiment, a plasticized hydrocarbon gel completes the carrier vehicle for tetracaine in any of the compositions described herein. The plasticized hydrocarbon gel may be mixture of polyethylene in mineral oil, such as light mineral oil (e.g., Jelene, available from Fagron, Inc.). The plasticized hydrocarbon gel keeps the paste from dissolving away quickly, giving tetracaine time to penetrate. In one embodiment of any of the compositions described herein, the plasticized hydrocarbon gel makes up about 70 wt. % to about 80 wt. %, such as about 75 wt. % or about 79 wt. %, of the composition.

In one embodiment, any of the compositions described herein may include one or preservatives. Preferably, if present, the preservative comprises no more than about 1 wt. % but may vary depending on the other components.

In one embodiment, any of the compositions described herein may include one or more odor masking agents. Suitable odor masking agents include, but are not limited to, peppermint oil, In one embodiment of any of the compositions described herein, the odor masking agent (such as peppermint oil) makes up about 0.1 wt. % to about 1 wt. %, such as about 0.6 wt. % to about 0.7 wt. %, of the composition.

In one embodiment, any of the compositions described herein has a pH of between about 8 and about 10, such as between 8.5 and about 9.5, such as about 9.

In one embodiment, the composition contains (a) from about 2 wt % to about 10 wt % of tetracaine base, (b) from about 2 to about 8 wt % sodium carboxymethyl cellulose, (c) from about 2 to about 10 wt % of polyethylene oxide (preferably having a molecular weight ranging from about 2,000,000 to about 6,000,000 Daltons), (d) from about 5 to about 15 wt % propylene glycol, (e) from about 65 to about 85 wt % plasticized base (such as a base comprising from about 92 to about 98 wt % mineral oil and about 2 to about 8 wt % polyethylene), and optionally (f) about 0.4 to about 1.0 wt % peppermint oil. Preferably, the sodium carboxymethyl cellulose has a viscosity in a 2% solution in water at 25° C. of 400-800 cps. In one preferred embodiment, the composition contains (a) from about 6 wt % of tetracaine base, (b) about 4 wt % sodium carboxymethyl cellulose, (c) about 5 wt % of polyethylene oxide (preferably having a molecular weight ranging from about 2,000,000 to about 6,000,000 Daltons), (d) about 10 wt % propylene glycol, (e) about 74 wt % plasticized base (such as a base comprising about 95 wt % mineral oil and about 5 wt % low molecular weight polyethylene), and optionally (f) about 0.7 wt % peppermint oil.

In one embodiment, the composition contains (a) from about 2 wt % to about 10 wt % of tetracaine base, (b) from about 2 to about 8 wt % sodium carboxymethyl cellulose, (c) from about 2 to about 10 wt % of polyethylene oxide (preferably having a molecular weight ranging from about 2,000,000 to about 6,000,000 Daltons), (d) from about 5 to about 15 wt % polyethylene glycol, (e) from about 65 to about 85 wt % plasticized base (such as a base comprising from about 92 to about 98 wt % mineral oil and about 2 to about 8 wt % polyethylene), and optionally (f) about 0.4 to about 1.0 wt % peppermint oil. Preferably, the sodium carboxymethyl cellulose has a viscosity in a 2% solution in water at 25° C. of 400-800 cps. In one preferred embodiment, the composition contains (a) from about 6 wt % of tetracaine base, (b) about 4 wt % sodium carboxymethyl cellulose, (c) about 5 wt % of polyethylene oxide (preferably having a molecular weight ranging from about 2,000,000 to about 6,000,000 Daltons), (d) about 10 wt % polyethylene glycol, (e) about 74 wt % plasticized base (such as a base comprising about 95 wt % mineral oil and about 5 wt % low molecular weight polyethylene), and optionally (f) about 0.7 wt % peppermint oil.

The topical anesthetic compositions of the present invention may be prepared using ordinary production methods. In one embodiment, the composition is prepared as described in Example 1.

The compositions may include the excipients and be prepared by the methods described in U.S. Pat. Nos. 8,263,047, 8,623,334, and 8,968,710, which are hereby incorporated by reference.

EXAMPLES

Example 1

A topical composition containing 6 wt. % tetracaine base having the formulation shown in the table below was prepared by mixing the appropriate components in the specified amounts.

| INGREDIENT | WEIGHT (% w/w) |
|---|---|
| Tetracaine USP Base | 6.0 |
| Sodium Carboxymethylcellulose USP, medium viscosity | 4.0 |
| PolyOx WSR 301 | 5.0 |
| Propylene Glycol USP | 10.0 |
| Plasticized Base (Jelene) (95% mineral oil and 5% low molecular weight polyethylene) | 74.33 |
| Peppermint Oil, NF | 0.67 |

The topical composition can be prepared as follows. Sodium carboxymethyl cellulose, PolyOx WSR 301, and tetracaine are ground in separate glass mortars to a fine powder and set aside. Ten percent extra tetracaine is weighed out because some of the tetracaine may adhere to the mortar. By starting with 10% extra, the ground tetracaine available for transfer results in a 6 wt. % composition.

Plasticized base (Jelene) is placed in a 200 ml beaker and the beaker placed directly onto a hotplate. The temperature of the hot plate is set on its lowest position. The plasticized base is gently heated until it became soft and semi-fluid. At which point, the plasticized base is workable for compounding purposes. plasticized base melts at about 82° F. Heating is stopped before the plasticized base totally melts as separation may occur and plasticized base may not resume its original consistency when cooled.

The ground sodium carboxymethylcellulose is added in small portions to the heated plasticized base with stirring after each addition to ensure a uniform mix. The beaker is removed from the heat and the mixture allowed to cool.

On an ointment slab, a portion of the finely ground tetracaine is worked with propylene glycol (25% of the total propylene glycol). The tetracaine and propylene glycol mixture is combined with a portion of plasticized base via geometric dilution. The cooled plasticized base and sodium carboxymethylcellulose mixture is then worked into the tetracaine, propylene glycol (25% of the total propylene glycol) and plasticized base mixture via geometric dilution.

In a glass mortar, the ground PolyOx WSR 301 is wetted with propylene glycol (75% of the total propylene glycol). The Polyox WSR 301 and propylene glycol mixture is then incorporated via geometric dilution with the other ingredients previously mixed together on the ointment slab to form the topical paste.

Example 2

A topical composition containing 2 wt. % tetracaine base having the formulation shown in the table below was prepared by mixing the appropriate components in the specified amounts. This composition can be prepared as described in Example 1.

| INGREDIENT | WEIGHT (% w/w) |
|---|---|
| Tetracaine USP Base | 2.0 |
| Sodium Carboxymethylcellulose USP, medium viscosity | 4.0 |
| PolyOx WSR 301 | 5.0 |
| Propylene Glycol USP | 10.0 |
| Plasticized Base (Jelene) | 78.33 |
| Peppermint Oil, NF | 0.67 |

Example 3

A 31 year old female patient presented with shingles in the active eruptive phase on her face, in her mouth, and on her cornea. The patient was currently taking 3 eye medications and valacyclovir (Valtrex). The patient was topically administered the topical composition of Example 1 three times a day. After seven days, the shingles was almost resolved and the patient had no pain. FIG. 1 shows the face of the patient prior to treatment (Day 0) and on Days 1-5 and 7 of treatment with the topical composition of Example 1.

Example 4

A 10 year old male patient presented with shingles on his arms. The patient was topically administered the topical composition of Example 1 three times a day. After five days, the shingles was almost completely resolved.

Figure 2A:
FIG. 2A shows the arms of the patient described in Example 4 at Day 0, prior to treatment with topical administration with the topical composition of Example 1.
Figure 2B:
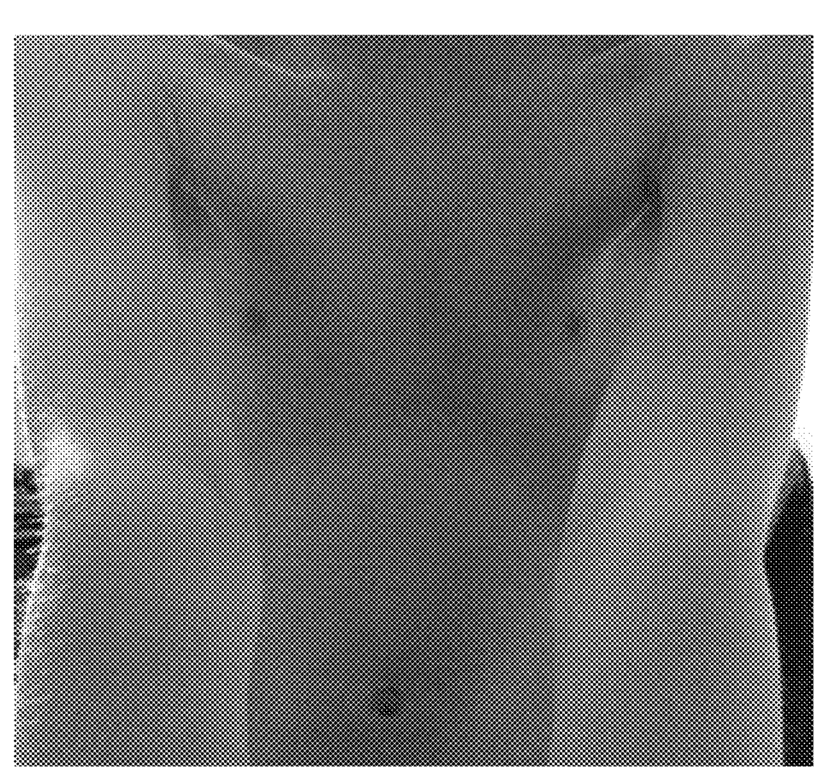
FIG. 2B shows the arms of the patient described in Example 4 after administration of the topical composition of Example 1 three times a day for five days.

FIG. 2A shows the arms of the patient at Day 0 (prior to treatment). FIG. 2B shows the arms of the patient after administration of the topical composition of Example 1 three times a day for five days.

Example 5

A 57 year old female patient presents with severe blisters on the left torso. The patient was topically administered the topical composition of Example 1 three times a day. Upon applying the topical composition of Example 1, the patient immediately felt no pain. After four days, the shingles was completely resolved.

Example 6

An 83 year old female patient presents with severe blisters on the left torso and in great pain. The patient was taking an antiviral and pain medication (acyclovir and oxycodone). The patient was then topically administered the topical composition of Example 1 three times a day. Upon applying the topical composition of Example 1, the patient immediately felt no pain. After seven days, the shingles was completely resolved.

Example 7

A topical composition containing 2 wt. % tetracaine base having the formulation shown in the table below was prepared by mixing the appropriate components in the specified amounts. This composition can be prepared as described in Example 1.

| INGREDIENT | WEIGHT (% w/w) |
|---|---|
| Tetracaine USP Base | 2.0 |
| Sodium Carboxymethylcellulose USP, medium viscosity | 4.0 |
| PolyOx WSR 301 | 5.0 |
| Polyethylene Glycol (PEG) 400 | 10.0 |
| Plasticized Base (Jelene) | 78.34 |
| Peppermint Oil, NF | 0.66 |

Example 8

Antiviral Evaluation of Tetracaine against Varicella Zoster Virus (VZV) in Skin Organ Culture with Varying Lengths of Treatment Time The goal of this study was to evaluate the effect of tetracaine against VZV in a skin organ culture (SOC) model and to determine an appropriate duration of treatment in skin to prevent VZV spread. Tetracaine, either the formulation of Example 2 or the formulation of Example 7, was tested as a topical treatment (formulated in the vehicle of Example 7) against VZV infections. Control formulations (cidofovir, CDV) were formulated in cocoa butter.

Figure 3:
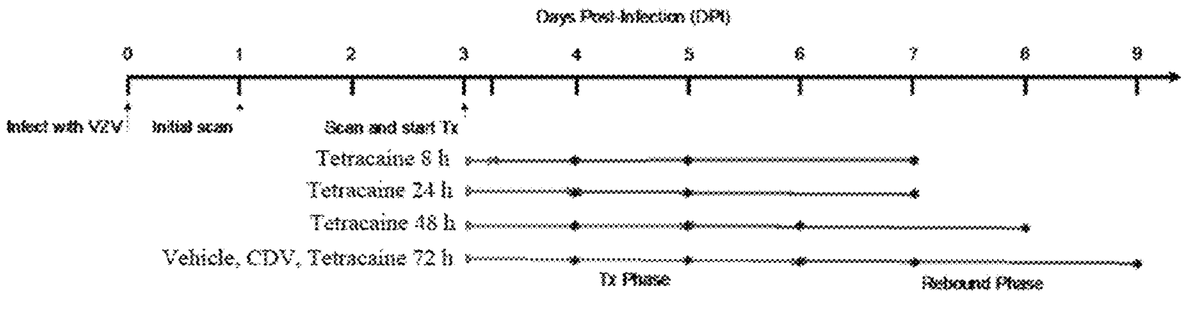
FIG. 3 shows the skin imaging timeline for the study described in Example 8.
Figure 4A:
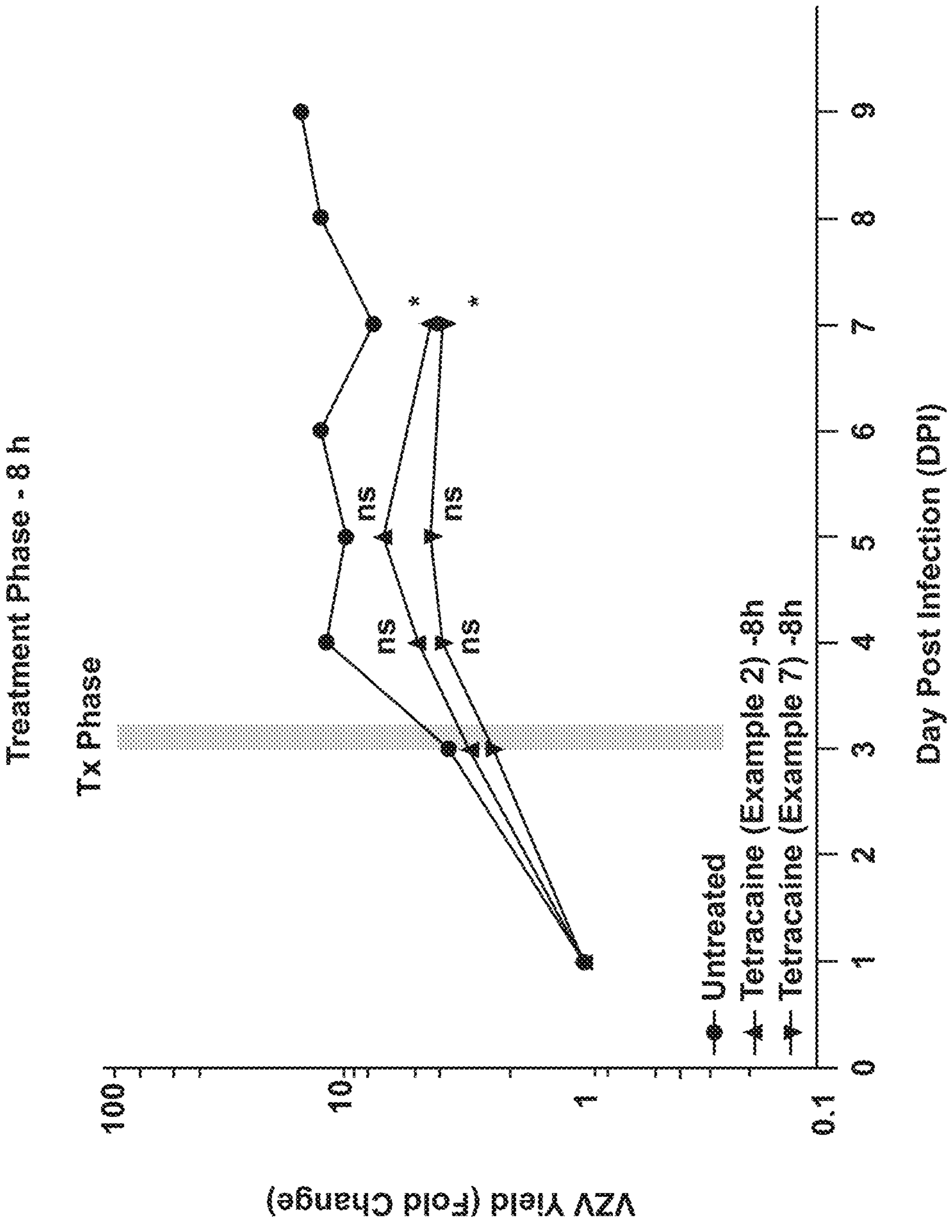
FIGS. 4A-4D show the Varicella Zoster Virus (VZV) yield as fold change after 8, 24, 48, and 72 hours of treatment, respectively, as described in Example 8.
Figure 4B:
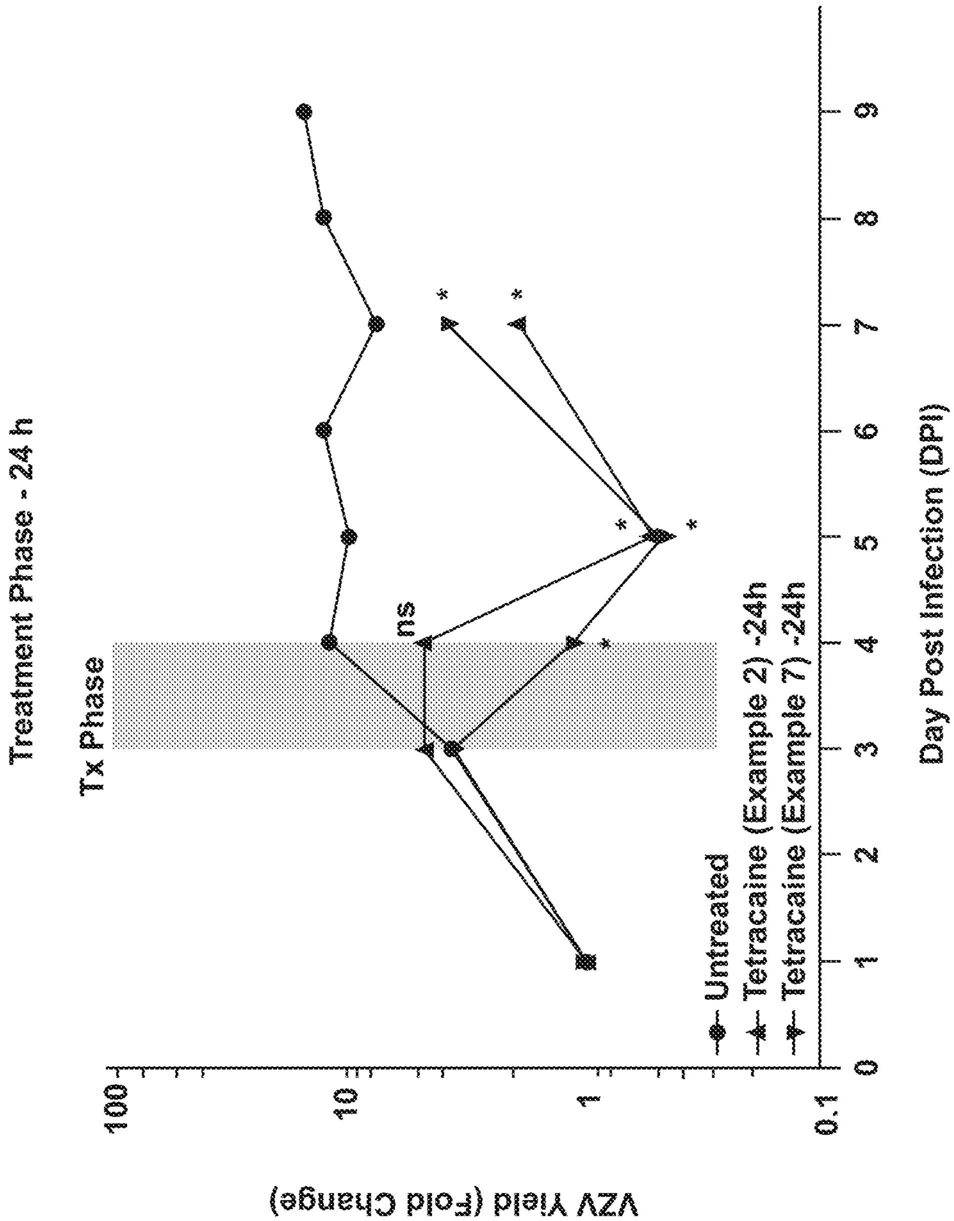
Figure 4C:
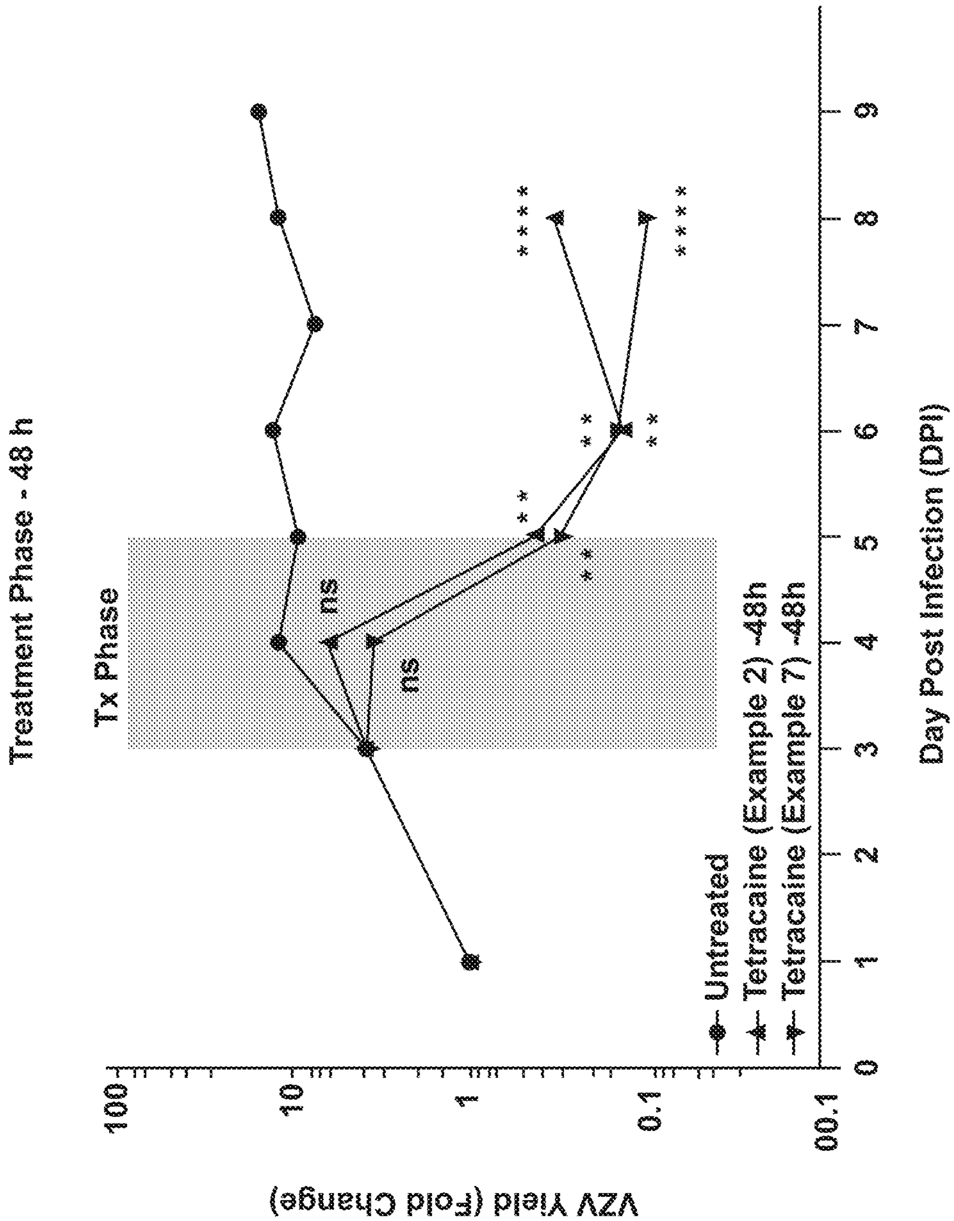
Figure 4D:
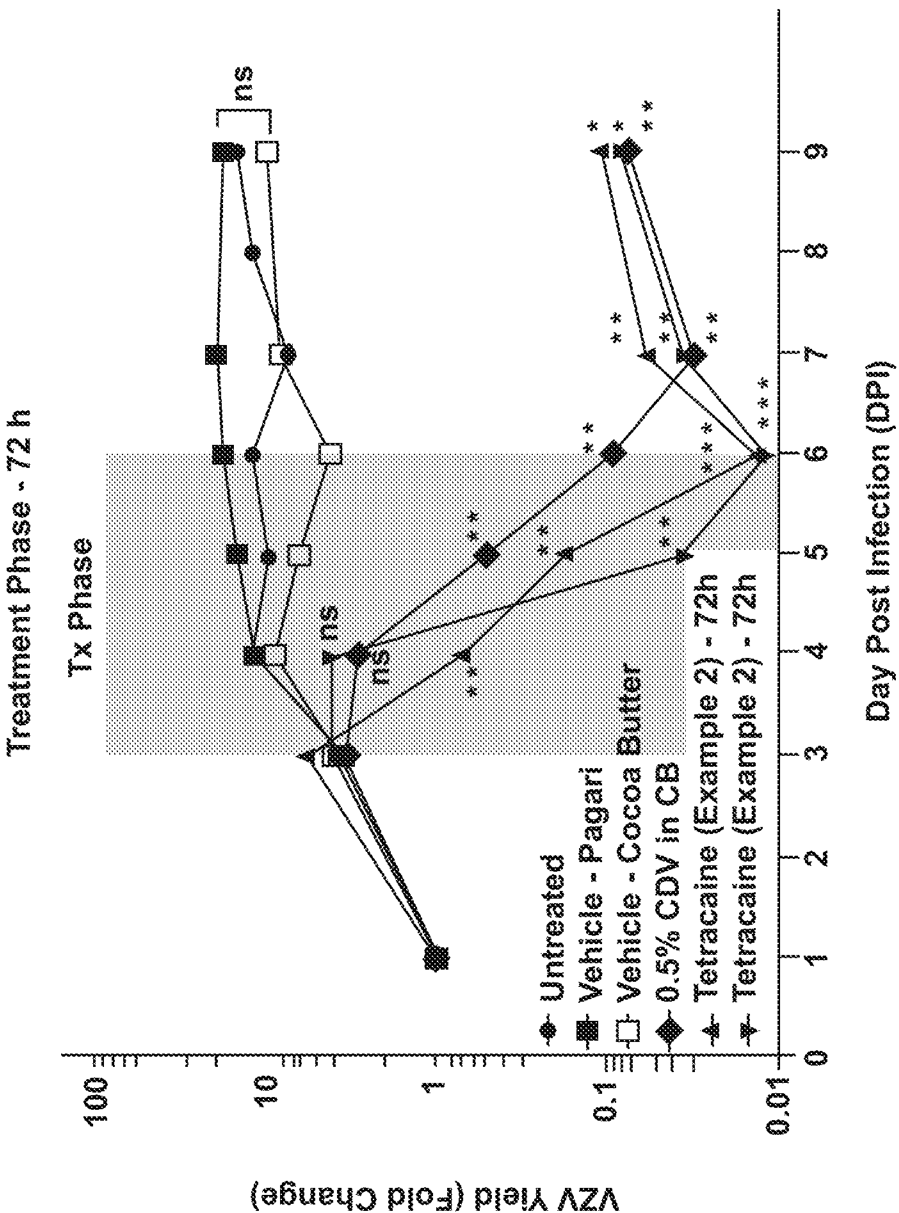

Adult human skin from a reduction mammoplasty was cleaned and cut to a thickness of 1 mm, maintaining normal skin architecture while removing underlying adipose and some of the subdermal and connective tissue. Skin was inoculated by scarification with VZV-ORF57-Luc (cell-associated virus, from a frozen stock). VZV-ORF57-Luc expresses firefly luciferase. Infected skin was placed on NetWells, which are designed to hold skin at the air-liquid interface. This orientation keeps the epidermis in contact with the air so it remains dry, while the dermis remains moist and in contact with the medium. Infected skin was scanned by IVIS Spectrum on DPI (Day Post Inoculation) 1 and 3, and prior to treatment being initiated. All treatments were started on DPI 3, but removed after different amounts of time, including after 8, 24, 48, or 72 hours. All compounds were formulated in either the test vehicle or cocoa butter (cidofovir, CDV) and applied directly to the epidermis. To remove treatment, the compound was gently wiped off the surface of the skin, and the entire skin explant was submerged and gently swirled in phosphate-buffered saline (PBS) for a few seconds to remove any residue. The topical treatment was removed prior to imaging by gently wiping it off the epidermis. The skin was imaged according to the timeline shown in FIG. 3.

FIGS. 4A-4D show VZV yield as fold change, which was calculated as the total flux (photons/sec) normalized to DPI 1 for each skin explant. Skin treatment started on DPI 3 and was removed based on the schedule shown in FIG. 3. Imaging started on DPI 1 and was performed every day or every other day starting on DPI 3, depending on the group. In FIGS. 4A-4D, the treatment period is highlighted by a gray box. The closed symbols on each graph also correspond to either the pre-treatment or treatment phases, whereas the open symbols correspond to the rebound phase (includes the 3 days after treatment ended).

Two different vehicles were used in this study. The first was formulated by the test vehicle (which was also used in Example 7) and the second was raw cocoa butter (vehicle cocoa butter). For these studies, the two different formulations of tetracaine were compared to the test vehicle by one-way ANOVA and the control compound, CDV, was formulated in cocoa butter and compared to the cocoa butter vehicle by a Student t-test. Initially, the fold change from the different vehicles to the untreated skin by one-way ANOVA was compared. Neither vehicle had a significant difference from the untreated group. CDV treatment caused significantly lower virus spread compared to the cocoa butter vehicle by the end of the treatment phase (see FIG. 4D, Student's t-test: **p<0.01). Tetracaine treatments of 24-72 hours were highly effective (one-way ANOVA: *p<0.05, p<0.01, *p<0.001, ****p<0.0001). However, 8 hour treatment with the formulation of Example 2 or Example 7 was not effective during the treatment period and immediately after (day 1 during rebound period). Surprisingly, by the third day of rebound, both 8 hour treatment groups were significantly lower than the vehicle group.

Figure 5:
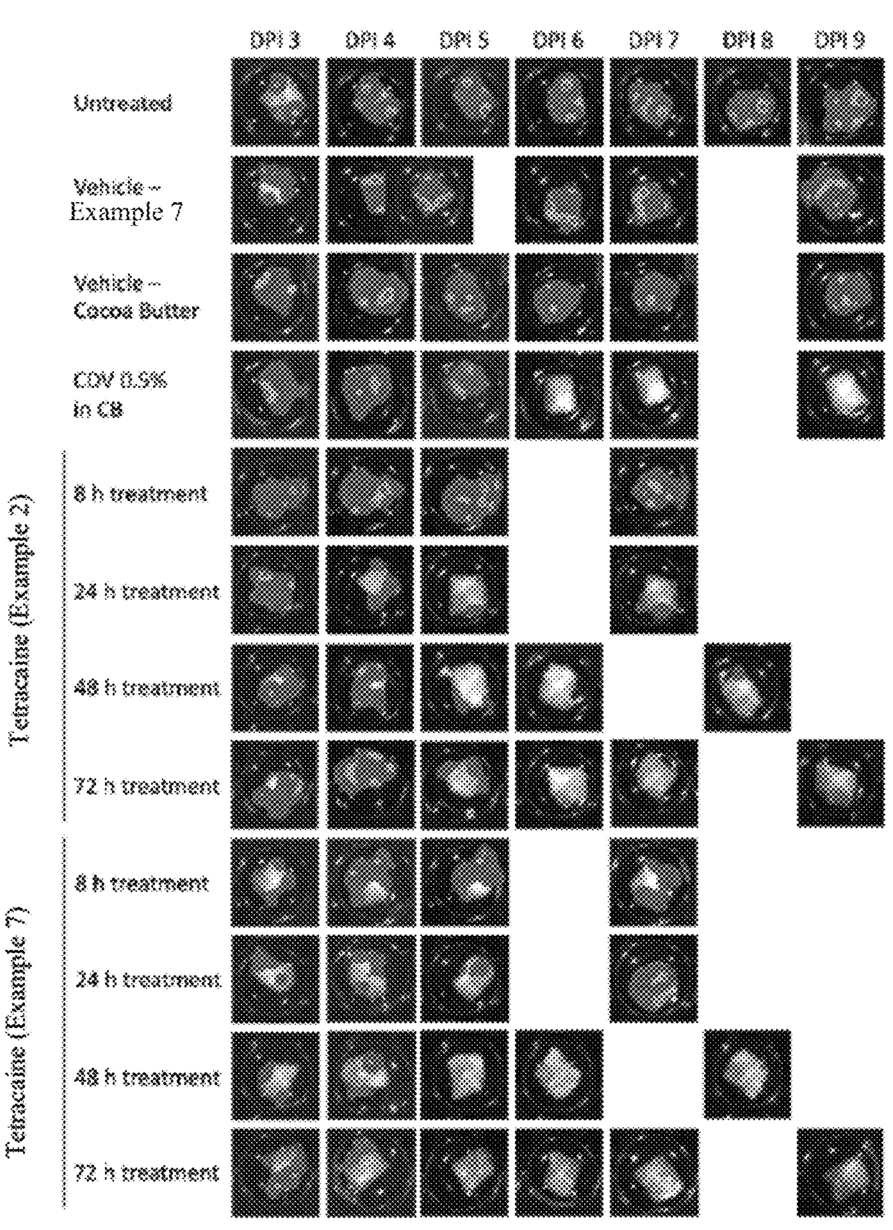
FIG. 5 shows bioluminescent images for skin samples treated in the study described in Example 8.

In this study, tetracaine was placed as a small drop in the center of the skin. A color change in the skin treated for 48 or 72 hours was observed, with more intense coloring in the 72 hour group. Interestingly, the skin was discolored only where tetracaine was applied. No color change to the skin treated with the vehicles or CDV was observed. FIG. 5 shows representative bioluminescent images of the skin in the untreated, Example 7 vehicle treated and tetracaine treated groups to show how treatment placed in the center still eliminated VZV present at the edges of the tissue. Each row in FIG. 5 depicts the same piece of skin over the course of the assay.

This study shows that tetracaine is highly effective against VZV-infected skin as a topical treatment. Low bioluminescent signals were detected in the treated skin explants even after 3 days, suggesting that tetracaine is highly effective but not toxic to the skin.

Figure 6:
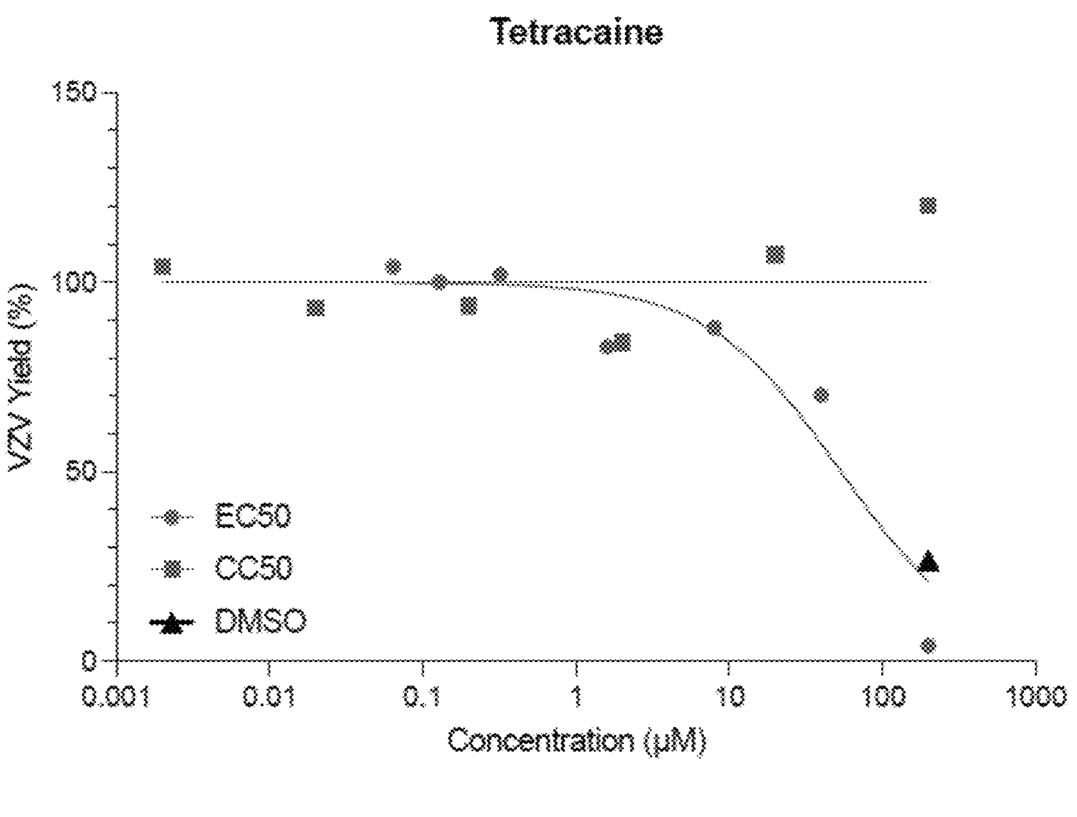
FIG. 6 shows calculated $EC_{50}$, $CC_{50}$ and SI ($CC_{50}/IC_{50}$) values for tetracaine and for dimethylsulfoxide (DMSO).

FIG. 6 shows calculated $EC_{50}$, $CC_{50}$ and SI ($CC_{50}/IC_{50}$) values for tetracaine, and data for 1% dimethylsulfoxide (DMSO) in the same vehicle but without tetracaine. The table below shows the calculated values for tetracaine.

| | $EC_{50}$ | $CC_{50}$ | SI |
|---|---|---|---|
| Tetracaine | 53.95 | >200 | 3.7 |

All references (including patents, patent applications, and literature) cited herein are hereby incorporated by reference in their entireties.

What is claimed is:

1. A method of deactivating varicella zoster virus in a patient in need thereof, where the patient suffers from herpes zoster, comprising topically administering to the patient a composition comprising (a) from about 2 wt. % to about 10 wt. % of tetracaine base or a pharmaceutically acceptable salt thereof, (b) from about 2 to about 8 wt. % sodium carboxymethyl cellulose, (c) from about 2 to about 10 wt. % of polyethylene oxide, (d) from about 5 to about 15 wt. % propylene glycol, (e) from about 65 to about 85 wt. % plasticized base, and optionally (f) about 0.4 to about 1.0 wt. % peppermint oil and wherein the tetracaine base is the sole active ingredient in the composition.

2. The method of claim 1, wherein the patient is in the active eruptive phase of herpes zoster when initially administered the composition.

3. The method of claim 1, wherein the patient exhibits lesions associated with herpes zoster in the active eruptive phase.

4. A method of deactivating varicella zoster virus in a patient in need thereof comprising topically administering to the patient an effective amount of a composition comprising (a) from about 2 wt. % to about 10 wt. % of tetracaine base or a pharmaceutically acceptable salt thereof, (b) from about 2 to about 8 wt. % sodium carboxymethyl cellulose, (c) from about 2 to about 10 wt. % of polyethylene oxide, (d) from about 5 to about 15 wt. % propylene glycol, (e) from about 65 to about 85 wt. % plasticized base, and optionally (f) about 0.4 to about 1.0 wt. % peppermint oil and wherein the tetracaine base is the sole active ingredient in the composition.

5. The method of claim 4, wherein the patient suffers from herpes zoster.

6. The method of claim 5, wherein the patient is in the active eruptive phase of herpes zoster.

7. A method of deactivating varicella zoster virus in a patient in need thereof, where the patient suffers from herpes zoster and is in the active eruptive phase of herpes zoster, comprising topically administering to the patient a composition comprising a) from about 2 wt. % to about 10 wt. % of tetracaine base or a pharmaceutically acceptable salt thereof, (b) from about 2 to about 8 wt. % sodium carboxymethyl cellulose, (c) from about 2 to about 10 wt. % of polyethylene oxide, (d) from about 5 to about 15 wt. % propylene glycol, (e) from about 65 to about 85 wt. % plasticized base, and optionally (f) about 0.4 to about 1.0 wt. % peppermint oil and wherein the tetracaine base is the sole active ingredient in the composition.

8. The method of claim 1, where the patient exhibits one or more symptoms associated with herpes zoster in the active eruptive phase.

9. The method of claim 8, wherein the one or more symptoms are selected from lesions, blisters, rash, mild to severe pain, pruritus, hyperesthesia, and any combination of any of the foregoing.

10. The method of claim 1, wherein the composition comprises from about 2 wt. % to about 10 wt. % of tetracaine base.

11. The method of claim 1, wherein the composition comprises from about 2 wt. % to about 10 wt. % of tetracaine hydrochloride.

12. The method of claim 1, wherein the poly(ethylene oxide) homopolymer has a molecular weight of about 4,000,000 daltons.

13. The method of claim 1, wherein the polyethylene oxide is present in an amount of about 5 wt. % and sodium carboxymethyl cellulose is present in an amount of about 4 wt. %.

14. The method of claim 1, wherein the composition comprises about 2 wt. % of tetracaine base.

15. The method of claim 1, wherein the composition comprises about 6 wt. % of tetracaine base.

16. The method of claim 1, wherein the composition is topically applied up to three times a day.

17. The method of claim 1, wherein tetracaine base is the sole active ingredient in the composition.

18. The method of claim 1, wherein the composition is topically applied and allowed to remain on the skin surface for a minimum of 8 hours.

* * * * *